United States Patent
Graze, Jr.

(10) Patent No.: US 7,533,585 B2
(45) Date of Patent: May 19, 2009

(54) DILUTION DEVICE

(75) Inventor: Russell Robert Graze, Jr., Dunlap, IL (US)

(73) Assignee: Caterpillar Inc., Peoria, IL (US)

( * ) Notice: Subject to any disclaimer, the term of this patent is extended or adjusted under 35 U.S.C. 154(b) by 175 days.

(21) Appl. No.: 11/646,923

(22) Filed: Dec. 27, 2006

(65) Prior Publication Data

US 2008/0156116 A1    Jul. 3, 2008

(51) Int. Cl.
*G01N 1/22* (2006.01)
(52) U.S. Cl. .................................. 73/863.21
(58) Field of Classification Search ............. 73/863, 73/863.21, 863.11, 863.12, 862.02, 863.03; 137/87.01, 88; 436/179
See application file for complete search history.

(56) References Cited

U.S. PATENT DOCUMENTS

| | | | | |
|---|---|---|---|---|
| 4,379,412 | A * | 4/1983 | Wood | 73/863.24 |
| 5,041,265 | A | 8/1991 | Koike et al. | 422/94 |
| 5,058,440 | A | 10/1991 | Graze, Jr. | 73/863.83 |
| 5,058,704 | A * | 10/1991 | Yu | 181/262 |
| 5,109,708 | A | 5/1992 | Lawless | 73/863.11 |
| 5,184,501 | A | 2/1993 | Lewis et al. | 73/23.31 |
| 5,297,432 | A | 3/1994 | Traina et al. | 73/864.34 |
| 5,567,390 | A | 10/1996 | Cleary | 422/111 |
| 6,615,677 | B2 | 9/2003 | Dickson et al. | 73/863.01 |
| 7,021,130 | B2 | 4/2006 | Schmidt | 73/114.69 |
| 7,044,009 | B2 | 5/2006 | Graze, Jr. | 73/863.03 |
| 7,328,629 | B2 * | 2/2008 | Farthing et al. | 73/863.11 |
| 2003/0213311 | A1 * | 11/2003 | Graze, Jr. | 73/864 |
| 2003/0232449 | A1 | 12/2003 | Mikkanen et al. | 436/179 |
| 2005/0084976 | A1 * | 4/2005 | Baldwin et al. | 436/81 |

FOREIGN PATENT DOCUMENTS

| | | |
|---|---|---|
| JP | 08-27237 | 10/1996 |
| JP | 2004205253 | 7/2004 |

* cited by examiner

*Primary Examiner*—Hezron Williams
*Assistant Examiner*—Tamiko D Bellamy
(74) *Attorney, Agent, or Firm*—Finnegan, Henderson, Farabow, Garrett & Dunner (57) ABSTRACT

A dilution device includes an inlet port and an outlet port. The dilution device also includes a first porous conduit defining an internal flow passage. The first porous conduit has a plurality of pores that communicate between an outside region external of the first porous conduit and the internal flow passage. The dilution device also includes a second porous conduit disposed around the first porous conduit. The second porous conduit defines a first chamber peripherally about the first porous conduit. The second porous conduit has a plurality of pores that communicate between an outside region external of the second pours conduit and the first chamber. The dilution device further includes a housing disposed around the second porous conduit. The housing defines a second chamber peripherally about the second porous conduit. The housing has an inlet port in communication with the second chamber. The first porous conduit includes a port at a first end of the first porous conduit in communication with the second chamber.

8 Claims, 6 Drawing Sheets

DILUTION DEVICE

TECHNICAL FIELD

The present disclosure relates to a dilution device for sampling gases, such as exhaust gases from engines or other effluent sources, and more particularly for sampling these gases to analyze particles contained therein.

BACKGROUND

With an increasing emphasis placed on protecting the environment, industries and governments are committing greater resources to monitoring and regulating existing stationary and non-stationary effluent sources as well as to developing new environmentally friendly stationary and non-stationary effluent sources.

For instance, exhaust gases or emissions from motorized vehicles are regulated by the U.S. Federal Government so as not to exceed certain maximum contaminant levels. Because of these regulations, increasingly more sophisticated testing equipment has been developed to test and analyze engines for conformance with such standards. As an example, regulations set by the U.S. Environmental Protection Agency (EPA) involve particulate limit standards for various types of engines such as diesel truck engines. The regulated particles are matter in the exhaust gas stream, other than condensed water, that can be collected after dilution. These particulates can include agglomerated carbon particles, absorbed hydrocarbons, and sulfates.

In order to comply with such regulations, industries involved in the manufacturing or use of effluent sources and government agencies responsible for enforcing such regulations have relied on systems that attempt to simulate the diluting process of the exhaust gases. Known methods include adding diluting air to the exhaust gas through a controlled sampling system that has a dilution tunnel. A significant challenge with these methods is the elimination of errors in measurements taken of the diluted exhaust gas and the diluting air streams and the need to precisely control their respective flow rates.

When the size of the effluent source, and more particularly, the mass flow of exhaust gas from the effluent source, permits, full sampling dilution systems may be used in which the total exhaust gas flow from the effluent source is mixed with a quantity of diluting air. However, when the size of the effluent source is so large that testing with a full sampling dilution system would not be practical due to the large size required for the corresponding dilution tunnel, proportional sampling dilution systems may be used in which only a portion of the exhaust gas flow is sampled, requiring a smaller dilution tunnel, along with reduced dilution air and exhaust mass flow requirements.

Investigations into the performance of all dilution system type used today continue to indicate excessive variability between governmental agencies, testing laboratories, and effluent source manufacturers. This variability can have negative consequences. On the one hand, the discrepancies between the testing laboratories may translate into competitive advantages for the low-result testing laboratories. On the other hand, the observed test-to-test variability translates into increased test expenditure because a large number of tests are required to obtain statistically significant results. Although there are several particle mechanisms that influence test-to-test variability, those most significant are particle deposition on the dilution tunnel and tailpipe walls by thermophoresis, by mechanical processes such as diffusion, gravitational sedimentation and turbulence, and by reentrainment of deposited particles and hydrocarbon gas phase exchange of the soluble portion of the exhaust particles with the deposited wall bound particles. Therefore, elimination of the deposition mechanism is highly desirable.

U.S. Pat. No. 5,058,440 discloses a dilution tunnel aimed at reducing the variability of test results in part through the elimination of thermophoretic deposition of particles on the walls of the sampling device and corresponding hydrocarbon gaseous phase component exchange with these wall-bound particles; down-sizing the dilution tunnel to produce a fully portable sampling system that can yield results equivalent to those of large testing laboratories; and a sampling system that can monitor variable engine operating parameters, automatically control the rate of exhaust gas withdrawal and vary the air dilution rate within preselected guidelines within a normal range of operating temperatures and pressures.

In particular, U.S. Pat. No. 5,058,440 discloses a gas sampling system that uses a dilution tunnel, including a sampling probe disposed in an exhaust gas stream of an engine, a source of clean diluting air, and a filter assembly. The dilution tunnel includes an air distribution conduit or diffuser conduit having a plurality of distribution holes therethrough, a porous center conduit having a plurality of micron-sized pores and defining a first chamber within the air distribution conduit, and a housing forming a second chamber about the air distribution conduit. The second chamber is connected to a diluting air source, and the center conduit is connected between a sampling probe in the exhaust gas flow and a filter assembly.

The known gas sampling systems, however, do not allow accurate simulations of a variety of diluting processes. Particularly, it is desired to have additional residence time for particle formation and growth. If a conventional residence chamber is attached to the tunnel, an artificial condition exists where residence time is increased without appropriate dilution ratio increase. This creates an artificial compositional change and growth in particle size compared to atmospheric processes.

The present invention is directed to overcoming one or more of the problems as set forth above.

SUMMARY OF THE INVENTION

In one aspect, the present disclosure is directed to a dilution device. The dilution device may include an inlet port and an outlet port. The dilution device may also include a first porous conduit defining an internal flow passage. The first porous conduit may have a plurality of pores that communicate between an outside region external of the first porous conduit and the internal flow passage. The dilution device may also include a second porous conduit disposed around the first porous conduit. The second porous conduit may define a first chamber peripherally about the first porous conduit. The second porous conduit may have a plurality of pores that communicate between an outside region external of the second pours conduit and the first chamber. The dilution device may further include a housing disposed around the second porous conduit. The housing may define a second chamber peripherally about the second porous conduit. The housing may have an inlet port in communication with the second chamber. The first porous conduit may include a port at a first end of the first porous conduit in communication with the second chamber.

In another aspect, the present disclosure is directed to a method of controlling fluid flow through an exhaust sampling system connected to a power source. The method may include extracting a portion of an exhaust flow of the power source, and directing the portion into a residence chamber of a dilution device. The method may further include directing dilute gas into the residence chamber through a porous wall surrounding the residence chamber. The method also include directing dilute gas through a porous conduit at central region of the residence chamber into the residence chamber, an directing a combined flow of the portion and the dilute gas out of the dilution device through an outlet port in communication with the residence chamber.

DETAILED DESCRIPTION

The invention relates to a dilution device for use in a gas sampling system to analyze particles in a sample gas, for example, taken from an engine exhaust. The dilution tunnel is configured to dilute the sample gas by introducing a diluting gas, such as clean air, into the sample gas. The diluted sample gas can then be analyzed to determine such characteristics as the amount and nature of the particles in the gas. The diluting process can be used in many applications, including, without limitation, the simulation of exhaust gases in the atmosphere from stationary or non-stationary sources.

Figure 1:
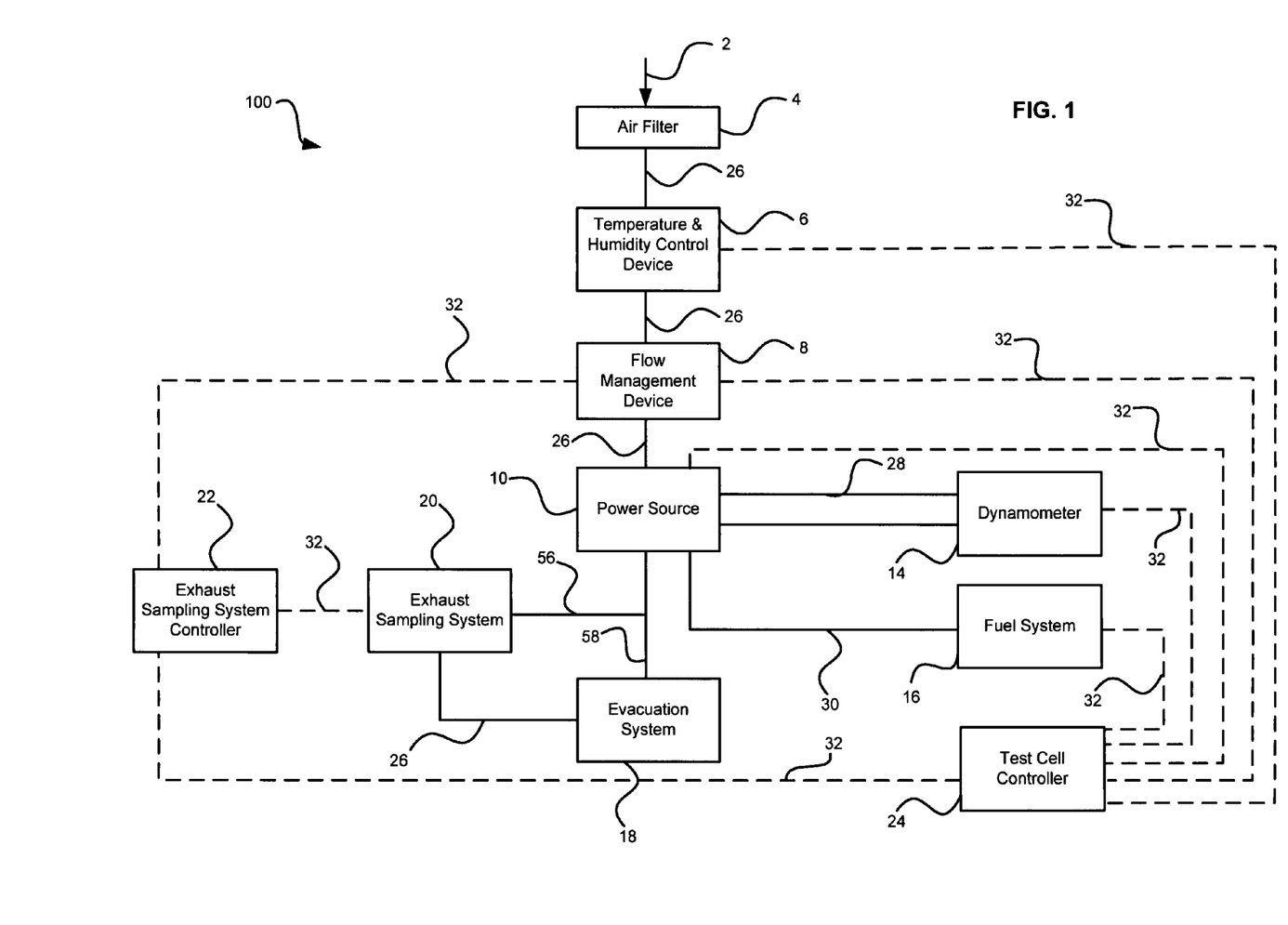
FIG. 1 is a diagrammatic illustration of a test cell according to an exemplary embodiment of the present disclosure.

FIG. 1 illustrates a test cell 100 according to an exemplary embodiment of the present disclosure. The test cell 100 includes a power source 10 mechanically and electrically coupled, and/or otherwise connected to a dynamometer 14. An air filter 4, a temperature and humidity control device 6, and a flow management device 8 may also be fluidly connected to, for example, an intake manifold of the power source 10. In addition, an exhaust manifold or other exhaust release device of the power source 10 may be fluidly connected to an evacuation system 18 of the test cell 100. The evacuation system 18 may include, for example, an exhaust fan and/or one or more filters configured to extract, for example, particulates and/or other harmful pollutants. The evacuation system 18 may also include, for example, a vacuum source or other device configured to act on exhaust gases from the power source 10 and/or an exhaust sampling system 20. The evacuation system 18 may be configured to release the exhaust gases to the environment.

As shown in FIG. 1, the exhaust sampling system 20 may be fluidly and/or otherwise connected to the power source 10, and an extraction tube 56 of the exhaust sampling system 20 may be configured to extract a portion of an exhaust flow of the power source 10. The exhaust sampling system 20 may include an exhaust sampling system controller 22 disposed within the test cell 100 and electrically connected to components of the exhaust sampling system 20 and/or the test cell 100. For example, the exhaust sampling system controller 22 may be configured to communicate electrically with the flow management device 8 and/or a test cell controller 24. As shown in FIG. 1 the power source 10 may also be fluidly connected to a fuel system 16 configured to supply fuel to the power source 10. Although not shown in FIG. 1, it is understood that the fuel system 16 may include, for example, a fuel pump, a fuel tank, a flow meter, a plurality of valves, and/or other conventional components configured to supply a regulated flow of fuel to the power source 10. These components may also be configured to measure, for example, the quantity, flow rate, and/or other characteristics of the flow of fuel supplied to the power source 10.

Figure 2:
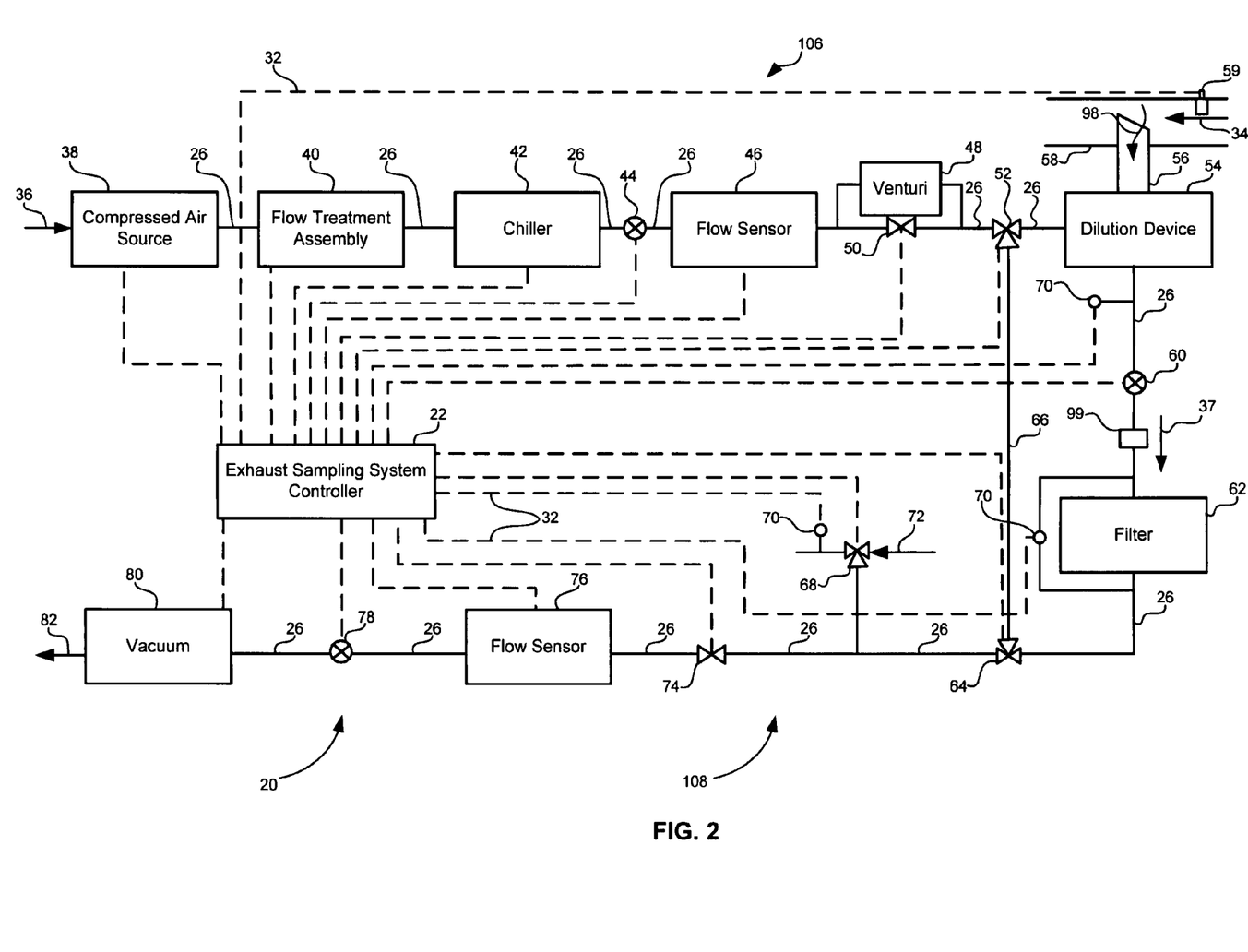
FIG. 2 is a diagrammatic illustration of a sampling system according to an exemplary embodiment of the present disclosure.

One or more of the components discussed above may be connected to each other via a flow line 26. For example, the air filter 4 may be connected to the temperature and humidity control device 6 via flow line 26, and the temperature in humidity control device 6 may be connected to the flow management device 8 via flow line 26. The fuel system 16 may be connected to the power source 10 via a fuel line 30 and the power source 10 may be connected to the evacuation system 18 via an exhaust line 58 (as shown in FIG. 2). In an exemplary embodiment, the fuel line 30 and the exhaust line 58 may be flow lines 26. The extraction tube 56 of the exhaust sampling system 20 may be connected to the exhaust line 58, and the extraction tube 56 may be configured to extract a portion 98 of an exhaust flow 34 of the power source 10 passing through the exhaust line 58. The exhaust sampling system 20 may also be connected to the evacuation system 18 via flow line 26, and the exhaust sampling system 20 may be configured to direct a flow of fluid to the evacuation system 18 during and/or after a sampling cycle. The power source 10 may also be connected to the dynamometer 14 via a mechanical and/or other conventional link 28.

As illustrated in FIG. 1 the temperature and humidity control device 6, the flow management device 8, the power source 10, the dynamometer 14, the fuel system 16, and/or the exhaust sampling system controller 22 may be electrically connected to the test cell controller 24 via control lines 32. In addition the flow management device 8 may be electrically connected to the exhaust sampling system controller 22 via a control line 32. Control lines 32 may enable each of the above components to communicate and/or otherwise send sensed information, control signals, and/or other electrical signals to the test cell controller 24 and/or the exhaust sampling system controller 22. Control lines 32 may also enable test cell controller 24 and/or exhaust sampling system controller 22 to send control signals to each of the connected components.

Power source 10 illustrated in FIG. 1 may be, for example, any spark ignition engine, diesel engine, and/or other source of mechanical or electrical power known in the art. Dynamometer 14 may be any conventional device used to measure, for example, rpm, torque, and/or other power source operating characteristics from which the output power produced by the power source can be calculated. Air filter 4 may be any conventional filter device configured to, for example, capture and/or otherwise trap dirt and other airborne particles before such particles pass to power source 10. Such particles may cause damage to, for example, power source cylinders, walls, pistons and piston rings. Air filter 4 may include, for example, a replaceable filter element configured to assist in the capture and/or removal of airborne particles.

Exhaust sampling system controller 22 and/or test cell controller 24 may be, for example, a central processing unit, an electronic control module, a computer, a radio transmitter, or any other type of controller known in the art. Controllers 22, 24 may be connected to an operator interface (not shown) such as, for example, a keyboard, monitor, printer, touch screen, control panel, or any other device enabling a user to enter commands and/or receive sensed and/or calculated information from components of test cell 100 and/or exhaust sampling system 20. In an exemplary embodiment, controllers 22, 24 may control aspects of the power source test/certification cycle and may be configured to store information for later retrieval and use.

Temperature and humidity control device 6 may be configured to sense and/or control the temperature and/or humidity of the filtered ambient air before it enters power source 10. Temperature and humidity control device 6 may include, for example, a thermocouple, a hygrometer, a heat exchanger, and/or other conventional components configured to assist in sensing and/or controlling temperature and humidity. Flow management device 8 may be any device or combination of devices configured to measure and/or regulate, for example, the flow rate, pressure, and/or other flow characteristics of a fluid flow. In an exemplary embodiment, flow management device 8 may include a laminar flow element and/or a pressure differential transducer configured to sense changes in the pressure and/or flow rate of a fluid passing through flow management device 8 and/or other components of test cell 100. Each of the test cell components discussed above is known in the art and these components will not be discussed in further detail in the present disclosure. Further, it is understood that each of the dash lines in FIG. 1 illustrate control line 32 and that each of the solid lines in FIG. 1 represents flow line 26 with the exception of extraction tube 56, exhaust line 58, and mechanical and/or other conventional link 28.

Referring now to FIG. 2, exhaust sampling system 20 in accordance with an exemplary embodiment of the present disclosure includes a dilute side 106 and a total side 108. A dilution device 54 of dilute side 106 may be fluidly connected to exhaust line 58 of power source 10 (FIG. 1), and dilute side 106 may further include, for example, a compressed air source 38, a flow treatment assembly 40, a chiller 42, a flow sensor 46, and a plurality of flow control and/or other types of valves. In addition, dilution device 54 of dilute side 106 may be fluidly connected to a filter 62 of total side 108, and total side 108 may further include, for example, a flow sensor 76, a vacuum 80, and a plurality of flow control and/or other types of valves 50. Exhaust sampling system controller 22 and/or test cell controller 24 (FIG. 1) may be electrically connected to one or more of the components of the exhaust sampling system 20. It is understood that each of the dash lines illustrated in FIG. 2 are control lines 32 and each of the solid lines connecting the components of exhaust sampling system 20 illustrated in FIG. 2 are flow lines 26.

As will be described in greater detail below, the components of dilute side 106 may be configured to compress, treat, cool, measure, and/or regulate a dilute flow 36 of ambient air. Dilute flow 36 may be combined with a flow of exhaust gas that is extracted from the exhaust flow of power source 10. In addition, the flow rate of dilute flow 36 may be rapidly adjusted by the dilute side components in response to the sensed difference between the flow rate of dilute flow 36 and the flow rate of the combined (dilute and extracted) flow.

Compressed air source 38 may include, for example, an air compressor or any other device capable of compressing a gas and delivering the compressed gas through flow lines 26. For example, in one embodiment of the present disclosure, compressed air source 38 may be an air compressor of a type known in the art and may supply compressed air at approximately 70 to 110 psi. This range may be increased or decreased. Compressed air source 38 may be configured to deliver a substantially constant, substantially uniform flow of compressed air to the components of exhaust sampling system 20. As illustrated in FIG. 2, dilute flow 36 may enter an intake of compressed air source 38 and may be compressed therein.

Compressed air source 38 may be fluidly connected to a flow treatment assembly 40 via flow line 26. Flow lines 26 of the present disclosure may be any type of tubing, piping, or hose known in the art. Flow lines 26 may be, for example, plastic, rubber, aluminum, copper, steel, or any other material capable of delivering a compressed gas in a controlled manner, and may be flexible or rigid. The length of flow lines 26 may be minimized to facilitate operation of exhaust sampling system 22, while reducing the pressure drop between the components thereof.

Flow treatment assembly 40 may be any assembly and/or collection of components configured to filter, treat, and/or otherwise clean dilute flow 36. In an exemplary embodiment, flow treatment assembly 40 may include a charcoal scrubber, an airflow drier that may be comprised of chemical desiccant or other drying means and/or a particulate filter (not shown). It is understood that the components of flow treatment assembly 40 may be separate devices disposed within a single housing. Alternatively, the components of flow treatment assembly 40 may be disposed in separate housings. The charcoal scrubber of flow treatment assembly 40 may be configured to remove, for example, hydrocarbons from the dilute flow 36. The air drier of flow treatment assembly 40 may be configured to remove, for example, water from dilute flow 36, and the particulate filter may be an ultra fine particulate filter of a type known in the art. Such particulate filters may be configured to capture and/or remove impurities contained within dilute flow 36, such as, for example, reentrained material from the chemical desiccant, charcoal from the charcoal scrubber, and/or any other airborne impurities. Flow treatment assembly 40 may be connected to chiller 42 via flow line 26.

Chiller 42 may be any device or combination of devices configured to reduce the temperature of a flow of fluid passing therethrough. Chiller 42 may be connected to, for example, a source of coolant to assist in reducing the temperature of the fluid flow passing therethrough. Chiller 42 may include, for example, a heat exchanger such as, for example, a radiator and/or any other conventional heat exchange device. In an exemplary embodiment of the present disclosure, chiller 42 may be configured to reduce the temperature of dilute flow 36 to approximately 20° C. Chiller 42 may be fluidly connected to a flow sensor 46 via flow line 26, and an isolation valve 44 may be disposed within flow line 26 between chiller 42 and flow sensor 46. It is understood that in an exemplary embodiment, compressed air source 38, flow treatment assembly 40, and/or chiller 42 may be independently controllable and, thus, may not be electrically connected to exhaust sampling system controller 22.

The isolation valve 44 may be any type of controllable fluid valve known in the art such as, for example, a poppet valve, a butterfly valve, or a ball valve. Isolation valve 44 may be controlled to completely restrict a flow of air from passing therethrough or may allow the flow to pass unrestricted. In an exemplary embodiment, isolation valve 44 may be a ball valve configured to substantially fully open and/or substantially fully close fluid communication between, for example, the chiller 42 and the flow sensor 46. The isolation valve 44 may be controlled by any conventional pneumatic and/or electric actuator such as, for example, a solenoid.

The flow sensor 46 may be any device and/or collection of devices configured to sense the volumetric flow rate and/or other characteristics of a flow passing therethrough. In an exemplary embodiment, the flow sensor 46 may include a laminar flow element configured to measure the volumetric flow rate of the dilute flow 36. The laminar flow element may include, for example, a matrix of small conduits in, for example, a honeycomb arrangement, and the laminar flow element may be any conventional type of laminar flow element known in the art.

In addition to the laminar flow element discussed above, the flow sensor 46 may further include one or more components configured to sense, for example, the pressure and/or temperature of the dilute flow 36 passing through the flow sensor 46. Such pressure and/or temperature measurements may be used to derive the density of the dilute flow 36. Thus, the exhaust sampling system controller 22 may use the volumetric output of the laminar flow element in conjunction with the density output of these additional components to determine, for example, the mass flow rate of the dilute flow 36.

The additional components of the flow sensor 46 may include, for example, a pressure differential transducer, an absolute pressure transducer, and a platinum resistance thermistor. Although these additional elements are not shown in FIG. 2 it is understood that the pressure differential transducer may include one or more pressure sensors disposed upstream and/or downstream of the laminar flow element and configured to measure a pressure drop across the laminar flow element. The absolute pressure transducer may be disposed upstream or downstream of the laminar flow element and may be configured to measure the absolute pressure of, for example, the dilute flow 36. In addition the platinum resistance thermistor may be disposed immediately upstream of an inlet of the laminar flow element and may be configured to sense the temperature of the dilute flow 36 entering the laminar flow element. The platinum resistance thermistor may be inherently stable due to the platinum and/or other metals utilized within the thermistor, and may be configured to make relatively fine and/or accurate temperature measurements.

The flow sensor 46 may be fluidly connected to the dilution device via a flow line 26, and a flow control valve 50 may be disposed in the flow line 26. The flow control valve 50 may be any type of controllable fluid valve known in the art configured to regulate a pressurized flow of fluid. The flow control valve 50 may be configured to rapidly respond to control signals sent from, for example, the exhaust sampling system controller 22.

The flow control valve 50 may be, for example, an electromagnetic valve having a plunger maintained in a magnetic field such that the mechanical resistance placed on the plunger is substantially zero while the flow control valve 50 is in use. The flow control valve 50 may be, thus, substantially instantly variable. The flow control valve 50 may have a response time of less than or equal to 75 milliseconds and may be configured to receive and react to substantially continuous flow commands sent by the exhaust sampling system controller 22. The flow control valve 50 may be configured to adjust the flow rate of the dilute flow 36 and/or the extracted flow according to the flow commands. The flow commands may be in response to, for example, the volumetric and/or mass difference between a combined flow 37 and the dilute flow 36.

The flow control valve 50 may also be configured to control the proportionality of the exhaust flow sample that is extracted from the exhaust flow of the power source 10 (FIG. 1). As used herein, the term "proportionality" is defined as the amount of exhaust flow that is extracted relative to the total exhaust flow 34 produced by the power source 10 at the time of the extraction.

In an exemplary embodiment of the present disclosure the exhaust sampling system 20 may further include a venturi 48. The venturi 48 may be, for example, a critical flow venturi or any other type of venturi known in the art. As illustrated in FIG. 2, venturi 48 may be arranged parallel to the flow control valve 50 such that an inlet of the venturi 48 may be fluidly connected downstream of an outlet of the flow sensor 46 and upstream of an inlet of the flow control valve 50. An outlet of the venturi 48 may also be connected to the flow line 26 downstream of an outlet of the flow control valve 50 and upstream of a valve 52. In an exemplary embodiment the venturi 48 may be sized and/or otherwise configured to receive approximately 80% of the maximum flow passing through a dilute side 106 of the exhaust sampling system 20. In such an embodiment the remaining 20% of the maximum flow traveling through the dilute side 106 may be controlled by the flow control valve 50. The venturi 48 may be configured to sense, for example, the flow rate and/or other characteristics of the dilute flow 36 passing through the dilute side 106 of the exhaust sampling system 20. The venturi 48 may be electrically connected to, for example, the exhaust sampling system controller 22 and may be configured to transmit, for example, sensed flow information thereto. It is understood that, in other exemplary embodiments of the present disclosure, the venturi 48 may be omitted. In such embodiments, the flow control valve 50 may be a single point of flow control.

An outlet of the flow control valve 50 may be fluidly connected to an inlet of the valve 52 via a flow line 26. The valve 52 may be a standard two-way valve, three-way valve, or any other type of controllable flow valve known in the art. In an exemplary embodiment, the valve 52 may be configured to direct the dilute flow 36 to pass from the dilute side 106 to a total side 108 of the exhaust sampling system 20 via a bypass line 66 for calibration and linearization of the flow measurement devices 46 and 76 relative to each other. In addition, the valve 52 may be configured to transmit the dilute flow 36 to an inlet 114 of dilution device 54 while substantially completely restricting flow from the dilute side 106 through the bypass line 66.

As discussed above in connection with FIG. 1, an extraction tube 56 of the dilution device 54 may be disposed within and/or fluidly connected to exhaust line 58. The extraction tube 56 may be configured to extract at least a portion of the exhaust flow 34 of the power source 10 during operation. The extraction tube 56 may be fluidly connected to the dilution device 54 such that the extracted portion of the exhaust flow 34 may be delivered to the dilution device 54 through the extraction tube 56.

The dilution device 54, which will be described in detail below, may be configured to receive the dilute flow 36 and may combine the dilute flow 36 with the extracted portion of the exhaust flow 34 discussed above, thereby diluting the extracted portion. An outlet of the dilution device may be fluidly connected to an inlet of the filter 62 via a flow line 26, and a valve 60 may be disposed in the flow line 26 between the dilution device 54 and the filter 62. The valve 60 may be, for example, an on/off valve, and the valve 60 may be mechanically similar to, for example, the isolation valve 44 discussed above. The valve 60 may be configured to substantially completely open or substantially completely close fluid communication between the dilution device 54 and the filter 62.

The filter 62 may be, for example, a particulate matter filter holder and/or any other type of exhaust flow particulate emissions measurement filter known in the art. Such types of filters may include, for example, treated high efficiency fiberglass-backed cellulose, quartz, Teflon (PTFE)-based, charcoal-impregnated cellulose, foam or other test filter media currently recognized in the state of the art for particulate emissions testing.

In an exemplary embodiment of the present disclosure, one or more diagnostic or auxiliary measurement devices 70 may be disposed proximate an inlet and/or an outlet of, for example the dilution device 54, the filter 62, and/or other components of the exhaust sampling system 20. The diagnostic devices 70 may be, for example, internal to or external from the components of the exhaust sampling system 20, and may be, for example, fluidly connected to one or more of the flow lines 26 of the exhaust sampling system 20. The diagnostic devices 70 may be any sensing devices known in the art such as, for example, flow meters, emission meters, particle size sensors, pressure transducers, radio devices, or other sensing and/or sampling devices configured to sense engine emissions. Such diagnostic devices 70 may sense, for example, soot and/or gaseous level, temperature, pressure, and/or other flow characteristics. Each of the diagnostic devices 70 may be electrically connected to the exhaust sampling system controller 22 and may be configured to send sensed information to the exhaust sampling system controller 22 via control lines 32. As shown in FIG. 2, in an exemplary embodiment, the diagnostic device 70 associated with the filter 62 may be, for example, a differential pressure transducer configured to sense the pressure drop across the filter 62. Such an exemplary diagnostic device may be fluidly connected proximate an inlet of the filter 62 and proximate an outlet of the filter 62.

In an exemplary embodiment of the present disclosure, one or more auxiliary measurement devices 99 may be disposed proximate the inlet of test filter 62. The auxiliary measurement devices 99 may be, for example, internal to or external from the components of the exhaust sampling system 20, and may be, for example, fluidly connected to one or more of the flow lines 26 of the exhaust sampling system 20. The auxiliary measurement devices 99 may be any sensing devices known in the art such as, for example, flow meters, emission meters, particle size sensors, pressure transducers, radio devices, or other sensing and/or sampling devices configured to sense engine emissions. Measurement devices 99 may sense, for example, soot, particle size, gaseous emissions concentration level, mass flow, temperature, pressure, and/or other flow characteristics. Each of the auxiliary measurement devices 99 may be electrically connected to the exhaust sampling system controller 22 and may be configured to send sensed information to the exhaust sampling system controller 22 via control lines 32. As shown in FIG. 2, in an exemplary embodiment, the auxiliary measurement device 99 may be, for example, a gaseous emissions concentration measurement system intended for use as an emission source development or certification tool.

In an exemplary embodiment of the present disclosure, the exhaust sampling system 20 may further include a thermistor 59. The thermistor 59 may be, for example, a resistor, a temperature sensitive semi-conductor, and/or any other type of temperature sensor known in the art. The thermistor 59 may be, for example, a fast response thermistor, and may include materials or components whose resistance changes rapidly when exposed to a change in temperature. As illustrated in FIG. 2, a component of the thermistor 59 may be fluidly connected to the exhaust line 58 and the thermistor 59 may be configured to sense changes in temperature of the exhaust flow 34 passing therethrough. The thermistor 59 may be electrically connected to, for example, the exhaust sampling system controller 22 and may be configured to transmit, for example, sensed temperature, flow, and/or other information thereto. It is understood that, in other exemplary embodiments of the present disclosure, the thermistor 59 may be omitted.

The dilute side 106 of the exhaust sampling system 20 may be connected to the total side 108 via bypass line 66 fluidly connecting the valve 52 to a valve 64. An outlet of the filter 62 may also be connected to the valve 64 via a control line 32. Accordingly, during use dilute flow 36 may be directed through the valve 52 to valve 64, via the bypass line 66, thereby bypassing, for example, the dilution device 54 and the filter 62. Alternatively, the dilute flow 36 may be directed through valve 52 to the dilution device 54 and the filter 62 before passing through the valve 64, and the valve 52 may prohibit flow from passing from the dilute side through the bypass line 66. As discussed above with respect to valve 52, the valve 64 may be, for example, a two-way valve, a three-way valve, or any other type of controllable flow valve known in the art. The valve 64 may be sized and/or otherwise configured to allow any range of flow to pass from the filter 62 to downstream components on the total side 108 of the exhaust sampling system 20. Accordingly, the valve 64 may be sized to handle larger flow volumes (i.e. combined flows) than the valve 52. An outlet of the valve 64 may be fluidly connected to an inlet of a flow control valve 74 via a flow line 26.

The flow control valve 74 may be structurally similar to the flow control valve 50 discussed above with respect to the dilute side 106 of the exhaust sampling system 20. As illustrated in FIG. 2, a flow line 26 may be fluidly connected between valve 64 and flow control valve 74. A valve 68 may be fluidly connected to the flow line 26 and configured to receive at least a portion of the flow exiting an outlet of the valve 64. The valve 68 may be any two-way or three-way valve known in the art. The valve 68 may be configured to allow a flow of ambient air 72 to pass through the flow line 26 to the flow control valve 74. Alternatively the valve 68 may be configured to receive a portion of the flow exiting valve 64 for sensing. A diagnostic device 70 may be fluidly connected to an outlet of the valve 68 to assist in sensing the flow received from valve 64.

In an exemplary embodiment, the diagnostic device 70 fluidly connected to the outlet of the valve 68 may be, for example, a flow meter sized to measure a flow through the valve 68. The flow through the valve 68 may be, for example, volumetrically analogous to the flow through the extraction tube 56. In such an exemplary embodiment, valve 52 and valve 64 may be controlled to direct a dilute flow 36 to valve 68, therefore bypassing the dilution device 54 and the filter 62. For example, during a quality control check, the flow sensor 76, the flow control valve 74, the flow sensor 46, the venturi 48, and the flow control valve 50 may be placed in series, and a flow potential may be created by the vacuum 80 and the compressed air source 38. In addition, during the exemplary quality control check, the flow through the flow sensor 46 may be set to, for example, 85 liters per minute and the flow through a flow sensor 76 may be set to, for example, 100 liters per minute. The difference between these two flows may be a flow of ambient air drawn through the valve 68 (represented by flow arrow 72). The volume of the flow of ambient air may be substantially the same as the flow of exhaust gas that would be extracted by the extraction tube 56 if the exhaust sampling system 20 was sampling exhaust gas. It is understood, however, that at any given time during operation, there is no simultaneous flow through the extraction tube 56 and through diagnostic device 70 proximate the valve 68.

It is understood that directly measuring the volume and/or other characteristics of the flow extracted from the power source exhaust flow by the extraction tube 56 may be difficult. For example, directly measuring the amount of flow extracted from the exhaust flow may quickly contaminate any flow meter, or other device used to measure the flow directly, with particulate matter. In addition, the extracted flow may have a temperature in excess of 600° C. and thus conventional flow meters may not be suitable for measuring such high temperature flows. Accordingly, due to the difficulties associated with measuring the extracted flow with an inline flow meter, directly measuring the expected extracted flow with the diagnostic device 70 prior or subsequent to an emissions test as a quality audit may be helpful.

An outlet of the flow control valve 74 may be fluidly connected to a flow sensor 76 via a flow line 26. The flow sensor 76 may be configured to measure, for example, the pressure, volume, mass, and/or other characteristics of the flow passing through the total side 108 of the exhaust sampling system 20. The flow sensor 76 may be any type of flow sensor known in the art. In an exemplary embodiment, the flow sensor 76 may be a volumetric device similar to the flow sensor 46 discussed above with respect to the dilute side 106. Thus, the flow sensor 76 may include a laminar flow element and a number of additional components configured to assist in calculating the mass flow passing through the flow sensor 76. Such components may include, for example, a platinum resistance thermistor and an absolute pressure transducer. It is understood that while a pressure transducer configured to measure pressure drop may be associated with the laminar flow element of the flow sensor 46, in an exemplary embodiment of the present disclosure, a corresponding pressure transducer may not be required to sense and/or measure the pressure drop across, for example, the flow sensor 76. In addition, as discussed above with respect to the flow sensor 46 the components of the flow sensor 76 may be configured to assist in defining the density of the flow passing through the flow sensor 76. Accordingly, the flow sensor 76 may configured to measure the mass of the flow passing therethrough.

In an exemplary embodiment, the flow sensor 76 may include a positive displacement type flow meter. Such a flow meter may include, for example, one or more sets of lobes disposed on meshed gears (not shown). Such gears may be constructed of, for example, aluminum, stainless steel, platinum, and/or any other like metals, and may be very finely machined so as to reduce friction and/or resistance between each other when meshing. In an exemplary embodiment, as flow is directed through the flow sensor 76, the internal lobes and/or gears may be moved and/or turned by the flow in direct proportion to the amount of flow being directed through the flow sensor 76.

An outlet of the flow sensor 76 may be fluidly connected to a valve 78 via a flow line 26. The valve 78 may be structurally similar to the isolation valve 44 discussed above with respect to the dilute side 106. Accordingly the valve 78 may be configured to substantially open and/or substantially close fluid communication between the flow sensor 76 and the vacuum 80 of the exhaust sampling system 20. The vacuum 80 may be any conventional source of negative pressure known in the art. The vacuum 80 may include, for example a shop vacuum, a vacuum pump, and/or any other device capable of creating negative pressure. The vacuum 80 may be of any power or capacity useful in drawing flow through an exhaust sampling system such as the exhaust sampling 20 illustrated in FIG. 2. In an exemplary embodiment of the present disclosure, the vacuum 80 may be configured to have a low pressure spike signature. Such a vacuum 80 may be configured to direct a substantially constant negative pressure to components of the exhaust sampling system 20.

Figure 3:
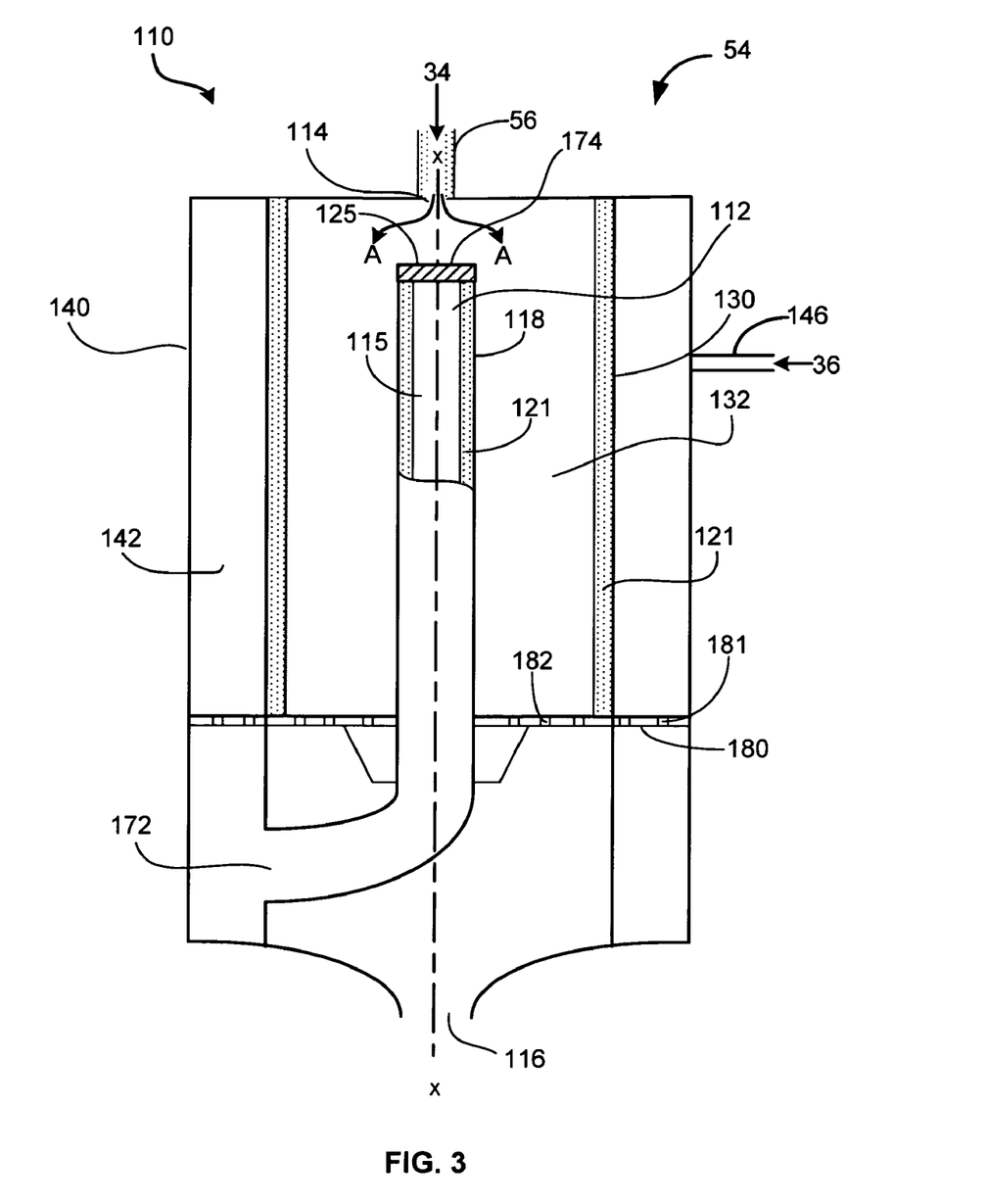
FIG. 3 shows a sample dilution device according to an exemplary embodiment of the present disclosure.

As shown in FIG. 3, in accordance with an exemplary embodiment of the present disclosure, the dilution device 54 includes a dilution tunnel 110. The dilution tunnel 110 may be fluidly connected to the extraction tube 56 such that the extracted portion of the exhaust flow 34 may be directed to the dilution tunnel 110.

As illustrated in FIG. 3, the dilution tunnel 110 may extend along a longitudinal axis X and may include a flow chamber structure that defines a porous conduit 112 extending between a first end 172 and a second end 174. As illustrated in FIG. 3, a cap 125 may be disposed at the second end 174 of the porous conduit 112 to block air flow at the second end 174.

The porous conduit 112 may include an internal flow passage 115 and a porous wall 118. Pores 121 (for example, but not limited to, about 0.5 micron in diameter) are formed in the wall 118 and communicate an outside region external of the porous conduit 112 with the internal flow passage 115 of the porous conduit 112. The porous conduit 112 may be made from a porous material, for example, sintered stainless steel having a plurality of pores that provide the desired precisely controlled porosity.

The dilution tunnel 110 may include a second conduit (diffuser conduit) 130 formed around the porous conduit 112, so as to define a first annular chamber (residence chamber) 132 peripherally about the porous conduit 112. The diffuser conduit 130 may be made from a porous material, for example, sintered stainless steel having a plurality of pores 121. Pores 121 may communicate an outside region external of the porous conduit 130 with the residence chamber 132.

The dilution tunnel 110 may also include a housing 140 that may form a second annular chamber (dilute flow chamber) 142 peripherally about the diffuser conduit 130. An inlet port 146 is formed radially through the housing 140 and may be in communication with a controlled flow rate source of dilute gas (e.g., the compressed air source 38 via the flow line 26) for receiving the dilute flow 36. As shown in FIG. 3, the porous conduit 112 may further include an inlet at the first end 172 in fluid communication with the dilute flow chamber 142, such that at least part of the dilute flow 36 may flow into the internal passage 115 of the porous conduit 112.

The porous conduit 112 may be secured within the dilution tunnel 110 by a plate 180, which is disposed across the residence chamber 132 and the dilute flow chamber 142. The plate 180 may include a plurality of holes 182 therethrough to allow particles and gas flow to pass through from the residence chamber 132 to an outlet 116. The portion of the plate 180 in the dilute air flow chamber 142 may also include holes 181 to allow dilute flow to pass through.

In use, the exhaust gas flow as denoted by arrows A may come from the extraction tube 56 to the residence chamber 132. The dilute flow may enter the dilution tunnel 110 from the inlet port 146 of the housing 140. After the dilute flow enters the dilution tunnel 110, part of the dilute flow may pass through the porous wall of the diffuser conduit 130 and may enter the residence chamber 132. The rest of the dilute flow may enter the internal passage 115 of the porous conduit 112 through the first end 172, and may emanate out of the porous conduit 112 to the residence chamber 132. In the residence chamber 132, the exhaust gas flow is diluted by the dilute flow coming from both ways. In one exemplary embodiment, the undiluted or partially diluted exhaust gas in residence chamber 132 cannot cross porous walls of diffuser conduit 130. Mixing and dilution occurs in residence chamber 132. The combined flow may then pass the holes 182 to the outlet 116. The outlet 116 of the dilution tunnel 110 may be fluidly connected to an inlet of the filter 62 via a flow line 26.

The residence chamber 132 may provide an environment where the exhaust gas may be sufficiently mixed with the dilute flow coming out from the central porous conduit 112 and coming in from the outer diffuser conduit 132, and thus being sufficiently diluted. The combined air flow may stay in the dilution tunnel 110 for a relatively long period of time, and the thermal phrase of the combined flow may change from a relatively hot condition to a relatively cold condition.

Figure 4:
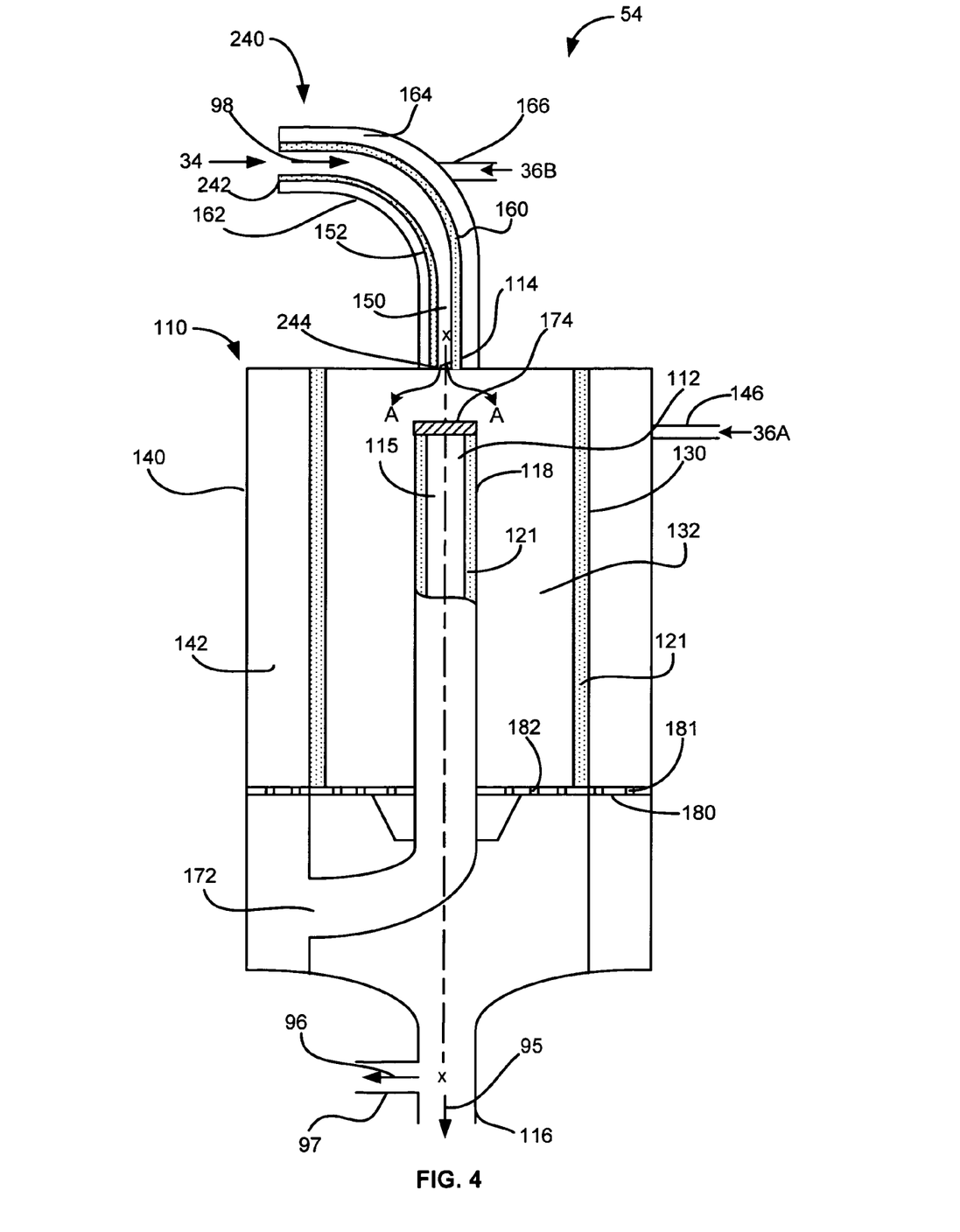
FIG. 4 shows a sample dilution device according to another exemplary embodiment of the present disclosure.

As shown in FIG. 4, according to another embodiment of the disclosure, the dilution device 54 may further include a dilute tunnel 240, for example, a curved tunnel, extending between an inlet port 242 and an outlet port 244 and connected with the above-described dilution tunnel 110 at the outlet port 244. The curved tunnel 240 may include an internal passage 150 defined by a porous wall 152. Pores 160 (for example, but not limited to, about 0.5 micron in diameter) are formed in the wall 152 and communicate an outside region external of the internal passage 150 with the inside of the internal passage 150. The curved tunnel 240 may include a housing 162 formed around the porous wall 152, so as to define an annular chamber (tunnel chamber) 164 located between the porous wall 152 and the housing 162. The housing 162 may include an inlet port 166 formed radially through the housing 162 and may be in communication with a controlled flow rate source of a dilute flow (e.g., the compressed air source 38 via the flow line 26). In one exemplary embodiment, the dilute tunnel 240 may function as the extraction component. The internal passage 150 may have the inlet port 242 facing an upstream direction of the exhaust gas flow 34. Thus, a proportionate sample of a particle-laden exhaust gas flow 34 may be directed to the interior of the internal passage 150. The internal diameter of internal passage 150 may or may not be constant throughout its length to vary the rate of the initial dilution process. In one exemplary embodiment, the undiluted or partially diluted exhaust gas in internal passage 150 cannot cross the porous wall 152. Mixing and dilution occurs in internal passage 150. The outlet 244 of the curved tunnel 240 may be connected to the dilution tunnel 110 as described above. The dilution tunnel 110 may provide further dilution to the combined flow coming from the curved tunnel 240.

In another exemplary embodiment, dilution device 54 may include curved tunnel 240 and dilution tunnel 110. Dilution tunnel 110 may further include a second outlet 97 in fluid communication with residence chamber 132, as shown in FIG. 4. In one embodiment, a combined flow 96 directed out of dilution device 54 through second outlet 97 may equal to dilute flow 36A directed into the dilution device 54 through inlet 146. The extracted flow 98, which is proportionally extracted from exhaust flow 34 and which is directed into the dilution device 54 through inlet port 242, plus dilute flow 36B directed into the dilution device 54 through inlet port 166 may equal to combined flow 95 extracted out of the dilution device 54 through outlet 116. In this exemplary embodiment, the combined flow 95 exited the dilution device 54 through outlet 116 may be maintained constant on a transient cycle, and the proportionality between extracted flow 98 to exhaust flow 34 may be maintained or changed by adjusting dilute flow 36B through inlet port 166. In some exemplary embodiments, the proportionality of extracted flow 98 may be maintained through control of dilute flow 36A through inlet 146, dilute flow 36B through inlet port 166, or a combination of both.

In some exemplary embodiments, dilution tunnel 110 may function only as a residence chamber connected to curved tunnel 240. In one exemplary embodiment, the dilute flow 36 may be directed into dilution device 54 only through the inlet port 166 of housing 162 of curved tunnel 240. No dilute flow is directed through inlet 146 of housing 140 of dilution tunnel 110 into dilution device 54. Therefore, the combined flow 37 through outlet 116 of dilution device 54 may be equal to the dilute flow 36 through inlet 166 plus the extracted flow 98 directed into inlet 242 of curved tunnel 240.

While the foregoing examples represent certain preferred geometric configurations for the dilution tunnel, they are not intended to be an exhaustive list of all the possible geometric configurations contemplated by the invention. Clearly, there remain numerous other possible configurations. For example, the porous member can be in the form of a cone expanding in the direction of exhaust gas flow. Still, the porous member, the diffuser conduit, and the housing may take on any other geometric configurations that permit variations in the diluting rate in the direction of exhaust gas flow, or that maintain a constant sampling proportionality rate under the given engine exhaust flow conditions.

INDUSTRIAL APPLICABILITY

The disclosed exhaust sampling system 20 including the dilution device 54 may be used with any diesel, gasoline, natural gas, and/or other internal combustion engines, furnaces, or power sources known in the art. As discussed above, the exhaust sampling system 20 may be used for testing, design, development, and/or certification of such power sources. It is understood that such power sources may be used in conjunction with any machine, on-road vehicle, off-road vehicle, stationary machine, and/or other exhaust producing devices known in the art.

A method for using the disclosed exhaust sampling system 20 to certify an exemplary power source will now be discussed with respect to the sampling strategy 184 illustrated in FIG. 5. It is understood that government regulations may require different testing scenarios depending upon the particular power source being certified. For example, some power sources may be certified under a steady state flow condition, while other power sources may be certified under transient flow conditions. As used herein, the term "transient flow condition" means flow conditions which are altered, modified, and/or otherwise changed during a test cycle. The exhaust sampling system 20 of the present disclosure may be used to certify power systems in both the transient and the steady state flow conditions. For the purposes of the present discussion, however, only a transient flow condition certification method will be discussed.

To begin using the exhaust sampling system 20 illustrated in FIG. 2, the user may bring the system 20 to thermal equilibrium. In thermal equilibrium, each component of the exhaust sampling system 20 may be at substantially the same temperature and, in an exemplary embodiment, the nominal temperature may be approximately 30 degrees Celsius. It is understood that, for example, the filter 62 and its components may be maintained at a temperature of approximately 47 degrees Celsius (plus or minus, approximately, five degrees Celsius) for certification purposes. Once thermal equilibrium has been reached, the user may keep the system running at idle until sampling begins. In order to achieve thermal equilibrium, the user may, for example, set a desired combined flow rate and a desired dilute flow rate. The desired dilute flow rate may correspond to the volume of dilute flow 36 that is to be directed to the dilution device 54 via the flow control valve 50. The desired combined flow rate may correspond to the volume of the combined flow 37 that is to be directed to the filter 62 on the total side 108 of the exhaust sampling system 20.

While the system is being brought to thermal equilibrium, the dilute flow 36 may pass through the compressed air source 38, the flow treatment assembly 40, the chiller 42, the open isolation valve 44, the flow sensor 46, and the open flow control valve 50. The valve 52 may then direct the dilute flow 36 through the dilution device 54 and may substantially fluidly seal the bypass line 66. In addition, the valve 60 may be substantially closed, thus, the dilute flow 36 may be directed through the extraction tube 56 to dislodge, for example, spurious particulate and/or other foreign matter that may have built up therein while the exhaust sampling system 20 was idle. The dilute flow 36 may then join the exhaust flow 34 and may be removed by the evacuation system 18 of the test cell 100. As illustrated in FIG. 2, a flow of gas 82 may be created by opening the valve 68 to allow a flow of ambient air to enter the valve 68, as illustrated by flow arrow 72. Alternatively, the operator can control the valves to extract a sample of the exhaust flow 34 and direct the sample through the filter 62. The operator may discard the filter media after extracting a sample during warm-up.

Figure 5:
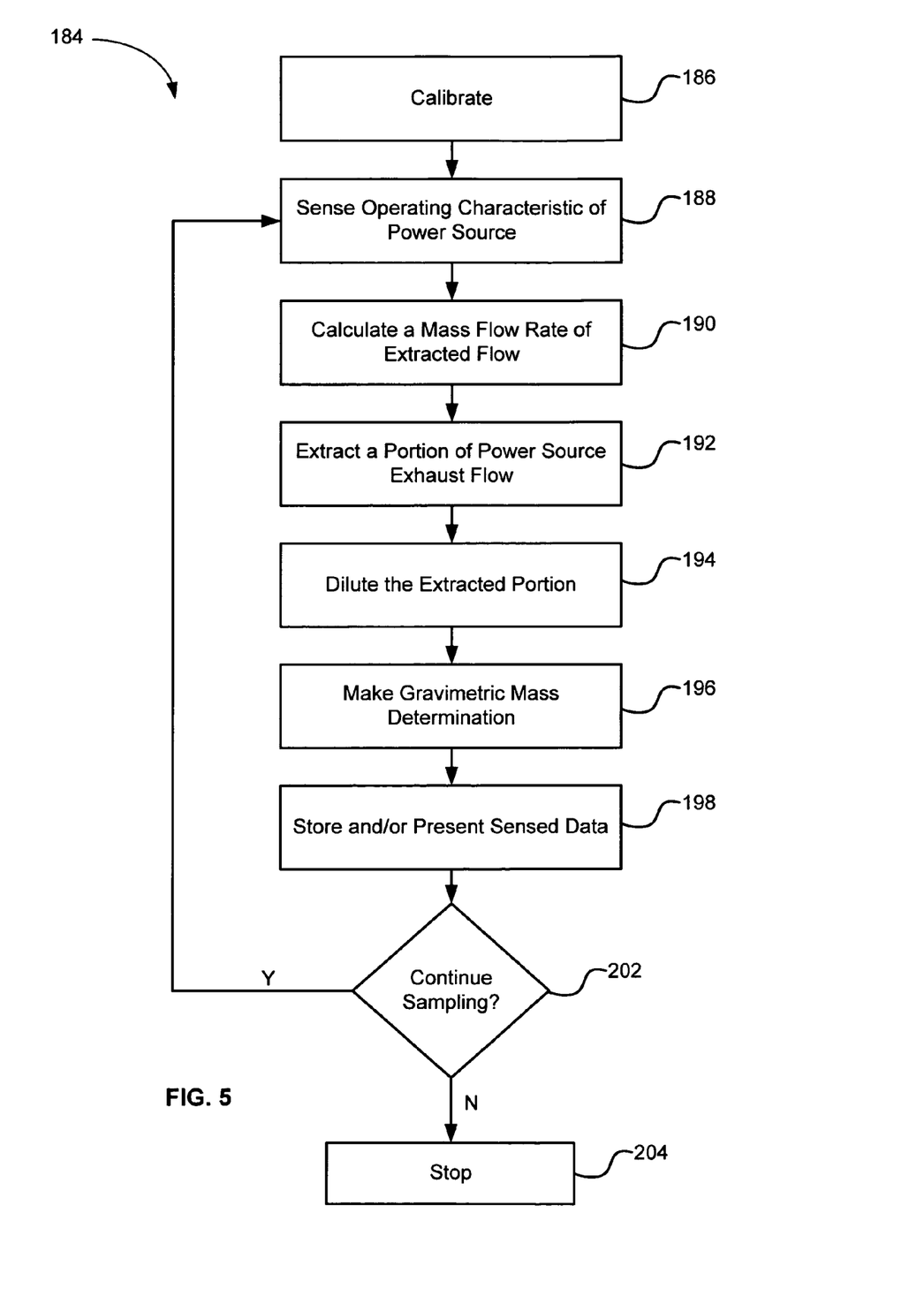
FIG. 5 shows a flow chart of a sampling strategy according to an exemplary embodiment of the present disclosure.

As shown in FIG. 5, once the exhaust sampling system 20 has reached thermal equilibrium, the user may calibrate the system (step 186). During calibration, the user may calibrate the dilute side 106 of the exhaust sampling system to the total side 108 in order to derive, for example, one or more polynomials for use in a control algorithm during sampling. In particular, during calibration the valve 44 and the flow control valve 50 may remain open and the valve 52 may direct the dilute flow 36 through the bypass line 66 to the valve 64. The dilute flow 36 may then pass through flow control valve 74 and the valve 68 may be fully closed such that none of the dilute flow 36 may pass through flow line 26. In such a configuration, the flow sensor 46 may be put in series with the flow sensor 76. The exhaust sampling system 20 may be operated throughout a series of flow points specified by the user. By using the flow sensor 46, the flow sensor 76, and/or other components of the exhaust sampling system 20 to measure the dilute flow 36 at each of the flow points, the exhaust sampling system controller 22 may calculate a polynomial that represents the relationship between the flow sensor 46 and the flow sensor 76. This polynomial may be used to mathematically correct the flow measurements made by the flow sensor 46 to the flow measurements made by sensor 76 during operation of the exhaust sampling system 20.

After calibration, the operator may install a test filter media cartridge into the filter 62 and may control the engine to a first test point using the test cell controller 24. At the first test point, one or more diagnostic devices 70 of the exhaust sampling system 20 and/or the test cell 100 may sense one or more operating characteristics of the power source 10 (step 188). Such operating characteristics may include, for example, the flow of air to an intake of the power source 10, the rate of fuel consumption, power source temperature, and/or the mass flow rate of the exhaust flow 34. Based on the sensed operating characteristics described above, the exhaust sampling system controller 22 may calculate a desired mass flow of the extracted flow (step 190). The calculated desired mass flow of the extracted flow may correspond to the desired amount of exhaust flow to be extracted from the exhaust flow 34. In addition, the desired extracted mass flow may be substantially proportional to the mass flow of the exhaust flow 34.

The exhaust sampling system controller 22 may then control the components of the exhaust sampling system 20 to extract the calculated desired portion of the exhaust flow 34 (step 192). The exhaust sampling system controller 22 may also control the compressor 38 flow treatment assembly 40, chiller 42, flow sensor 46 and/or flow control valve 50 to direct a dilute flow 36 to the dilution device 54 in order to dilute the extracted portion of the power source exhaust flow (step 194). It is understood that, as used herein, the term "dilution" means mixing a flow of extracted exhaust with a flow of ambient air so as to simulate environmental conditions such as pressure and/or temperature. It is understood that during operation of the exhaust sampling system 20 the components of the exhaust sampling system 20 may operate at relatively high dilution ratios (i.e., the flow rate of the dilute flow 36 relative to the flow rate of the extracted flow 98 may be relatively high). Such high dilution ratios may be required in order to reduce the temperature of the extracted flow to approximately 52° C. before the combined flow 37 reaches the filter 62.

During use, the exhaust sampling system 20 may substantially continuously and substantially instantly control the difference between the combined flow 37 and the dilute flow 36 with the flow control valves 74, 50 respectively. By controlling the difference between the flows 37, 36 in this way, the user may control, for example, the volume of the flow 98 that is extracted from the exhaust flow 34 because the volume of the combined flow 37 is equal to the volume of the dilute flow 36 plus the volume of the extracted flow 98. In one exemplary embodiment, exhaust flow 34 may be measured. Alternatively, exhaust flow 34 may be calculated based measured engine intake airflow or engine intake airflow plus fuel flow. By controlling the difference between the combined flow 37 and the dilute flow 36, the user may accurately control the proportionality of the extracted flow 98 to the exhaust flow 34 during a transient test cycle. Such a control strategy may be advantageous since it takes into account excursions in the exhaust flow 34 without directly sensing, for example, the mass flow rate and/or other characteristics of the exhaust flow 34 or the extracted flow. In addition, such a control strategy avoids the difficulties of directly measuring such flows discussed above.

The exhaust sampling system 20 may be controlled to ensure that the instantaneous difference between the total side mass flow and the dilute side mass flow is continually proportional to the power source exhaust mass flow. In order to achieve this, the exhaust gas sampling system controller 22 may be configured to continually monitor the operating characteristics of the power source 10 described above with respect to step 188, and calculate system flow set points which yield proportional sampling. In particular, in transient certification trials in which the exhaust flow rate changes, the components of the exhaust sampling system 20 may be configured to react to those changes within less than or equal to 500 milliseconds.

The combined flow 37 may pass from the dilution device 54 to the filter 62, whereby the particulates contained within the combined flow 37 may be extracted and trapped within the filter media. The filtered combined flow 37 may then pass from the filter 62, through valve 64, and through the flow control valve 74 to the flow sensor 76 where a gravimetric mass determination may be made (step 196). Sensed information may be transmitted from one or more components of the flow sensor 76 to the exhaust sampling system controller 22, and the exhaust sampling system controller 22 may store and/or present the sensed data to the operator or user (step 198).

The combined flow 37 may then pass from the flow sensor 76, through the open valve 78, and to the vacuum 80. The combined flow 37 may exit the exhaust sampling system 20 as illustrated by flow arrow 82. Once an adequate amount of data has been collected and/or stored by the exhaust sampling system controller 22, the exhaust sampling system controller 22 may determine whether or not continued sampling may be required for the purposes of certification (step 202). If continued sampling is required, the exhaust sampling system controller 22 may continue to sense operating characteristics of the power source 10 as described above (step 188). Alternatively, if a sufficient amount of data has been acquired the exhaust sampling system controller 22 may stop sampling (step 204). It is understood that in a transient certification procedure, the user may operate the power source 10 through a variety of different throttle and/or other set points. During such a procedure, the operating characteristics of the power source 10 may be continuously sensed or determined, for example, based on the engine intake air flow rate. The flow rate of the dilute flow 36 delivered to the dilution device 54 may be continuously changed in response to the sensed operating characteristics of the power source 10, as well as the sensed flow rate of the combined flow 37 passing through the total side 108 of the exhaust sampling system 20.

It is understood that, in an exemplary embodiment, the exhaust sampling system 20 may also be controlled to slow its transient response in applications where a relatively low output power source 10 is connected to a relatively large volume exhaust system, such as, for example, one or more relatively large volume components of the test cell 100. During use, the thermistor 59 may sense changes in the temperature of the exhaust flow 34 and may send the sensed temperature information to the exhaust sampling system controller 22. The exhaust sampling system controller 22 may calculate the volumetric flow rate of the exhaust flow 34 based on, for example, the temperature input received from the thermistor 59 and the mass flow rate of the exhaust flow 34 discussed above. In an exemplary embodiment, the exhaust sampling system controller 22 may calculate the volumetric flow rate at approximately 80 Hz, and the test cell operator may input the volume of the exhaust system based on the length and diameter of, for example, the exhaust line 58. If the time it takes for a particle to travel in the exhaust flow 34 between, for example, the power source 10 and the extraction tube 56 exceeds the known response time of the exhaust sampling system 20, the exhaust sampling system controller 22 may delay the proportional response of the exhaust sampling system 20 through control of, for example, the flow control valve 50. For example, if the known response time of the exhaust sampling system 20 is 200 milliseconds and the calculated travel time of a particle between the power source 10 and the extraction tube 56 is 300 milliseconds at a given instant, the exhaust sampling system controller 22 may delay a transient response by the exhaust sampling system 20 by 100 milliseconds.

Other embodiments of the disclosed exhaust sampling system 20 will be apparent to those skilled in the art from consideration of the specification. For example, the isolation valve 44 and the valve 78 may be three way valves configured to direct a flow of fluid from a flow line 26 to other locations within the exhaust sampling system 20. In addition, the filter 62 may be fitted with one or more bosses to assist in inserting and/or removing the test filter media cartridge.

Figure 6:
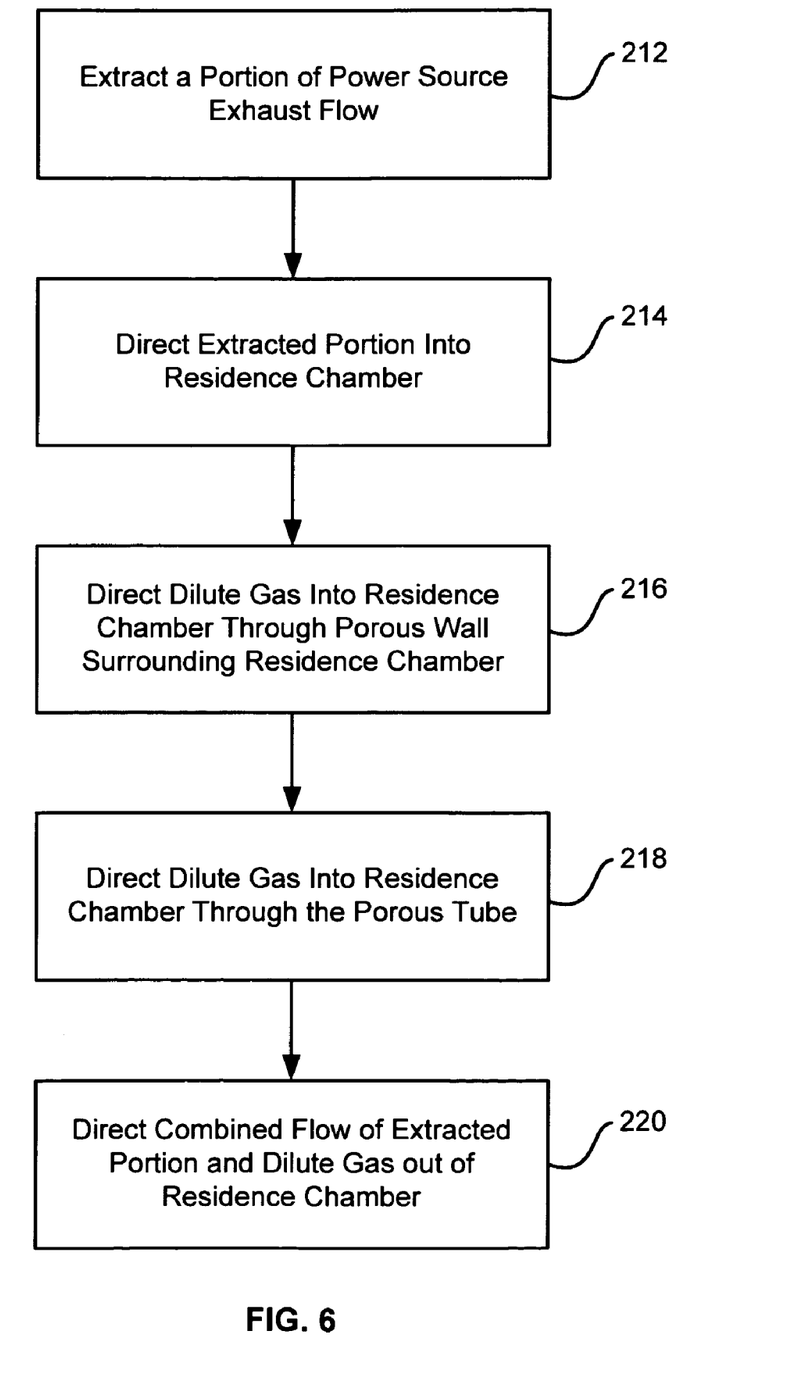
FIG. 6 shows a flow chart illustrating an exemplary disclosed method of diluting a flow of exhaust gas according to an exemplary embodiment of the present disclosure.

FIG. 6 illustrates an exemplary method of diluting the extracted portion of the power source exhaust flow. At step 212, a portion 98 of the exhaust flow 34 of power source 10 may be controllably extracted by the extraction tube 56 of the dilution device 54. At step 214, the extracted portion may be directed into residence chamber 132 of dilution device 54. At step 216, dilute gas is directed through the inlet port 146 into the second chamber 142. The dilute gas may pass through the porous conduit 130 into residence chamber 132. Part of the dilute gas may enter the porous conduit 112 through the first end 172. The dilute gas entering the porous conduit 112 may emanate through the porous wall 118 into the residence chamber 132 (step 218). The extracted portion may mix with the dilute gas within the residence chamber 132 coming from the central porous conduit 112 and coming from the outer porous conduit 130. At step 220, a combined flow of the exhaust gas and the dilute flow may flow out of the dilution device 54 through outlet port 116 in communication with the residence chamber 132.

The dilution tunnel of this disclosure provides several advantages over the conventional dilution tunnels. In particular, the dilution tunnel of this disclosure provides additional residence time for particle formation and growth. The arrangement of the residence chamber provides an environment where the residence time is increased with appropriate dilution ratio increase. Thereby, a better simulation of an atmospheric process of dilution can be achieved. By adding the second set of flow apportionment and control devices, the rate of diffusional dilution can be changed easily and over a wide range. This adds degrees of freedom for carrying out different dilution processes in an accurate and cost-effective manner.

It will be apparent to those skilled in the art that various modifications and variations can be made to the dilution device and the sampling system. Other embodiments will be apparent to those skilled in the art from consideration of the specification and practice of the disclosed dilution device and the sampling system. It is intended that the specification and examples be considered as exemplary only, with a true scope being indicated by the following claims and their equivalents.

What is claimed is:

1. A dilution device, comprising:
a first fluid inlet port and a combined fluid outlet port;
a first porous conduit defining an internal flow passage, the first porous conduit having a plurality of pores that communicate between an outside region external of the first porous conduit and the internal flow passage;
a second porous conduit disposed around the first porous conduit, a first chamber located between the second porous conduit and the first porous conduit, the second porous conduit having a plurality of pores that communicate between an outside region external of the second pours conduit and the first chamber; and
a housing for a dilution device enclosing the first and second porous conduits, the housing defining a second chamber at least partially around the second porous conduit, the housing having a second fluid inlet port in communication with the second chamber,
wherein the first porous conduit includes a port at a first end portion of the first porous conduit in communication with the second chamber.

2. The dilution device according to claim 1, wherein the first fluid inlet port of the dilution device is in fluid communication with a first fluid extraction component.

3. The dilution device according to claim 1, further including a second outlet in fluid communication with the first chamber.

4. The dilution device according to claim 1, further including a tunnel coupled to the first fluid inlet port of the dilution device, the tunnel including an internal passage defined by a porous wall and a housing formed around the porous wall and defining a tunnel chamber at least partially around the porous wall, the housing of the tunnel having an inlet in communication with the tunnel chamber.

5. The dilution device according to claim 1, further including a cap disposed at a second end portion of the internal flow passage of the first porous conduit.

6. The dilution device according to claim 1, further comprising a plate disposed across the first chamber, wherein the plate includes a plurality of holes therethrough.

7. The dilution device according to claim 1, wherein the second fluid inlet port of the housing is fluidly connected to a flow control valve configured to control a flow of second fluid into the dilution device.

8. The dilution device according to claim 1, further comprising a flow sensor fluidly connected downstream of the dilution device and configured to sense a characteristic of a combined fluid flow, and a controller configured to control a mass flow rate of a flow of first fluid extracted by the dilution device based on the sensed characteristic of the combined flow.

* * * * *